United States Patent [19]

Broomé

[11] Patent Number: 5,122,149
[45] Date of Patent: Jun. 16, 1992

[54] SURGICAL INSTRUMENT

[75] Inventor: Albert Broomé, Helsingborg, Sweden

[73] Assignee: Astra Meditec AB, Molndal, Sweden

[21] Appl. No.: 780,842

[22] Filed: Oct. 23, 1991

Related U.S. Application Data

[63] Continuation of Ser. No. 544,039, Jun. 26, 1990, abandoned, which is a continuation of Ser. No. 246,697, Sep. 20, 1988, abandoned.

[30] Foreign Application Priority Data

Sep. 30, 1987 [SE] Sweden ............................ 8703760

[51] Int. Cl.⁵ .................................................. A61B 17/12
[52] U.S. Cl. ................................................... 606/140
[58] Field of Search ..................... 606/140, 141, 165; 128/831, 843

[56] References Cited

U.S. PATENT DOCUMENTS

| | | | |
|---|---|---|---|
| 3,382,873 | 5/1968 | Banich et al. | |
| 3,760,810 | 9/1973 | Van Hoorn | |
| 3,889,657 | 6/1975 | Baumgarten | 128/304 X |
| 4,257,419 | 3/1981 | Goltner et al. | |
| 4,267,839 | 5/1981 | Laufe et al. | 606/141 |
| 4,735,194 | 4/1988 | Stiegmann | 128/303 A X |
| 4,760,848 | 8/1988 | Hasson | 128/321 |

Primary Examiner—Michael H. Thaler
Attorney, Agent, or Firm—White & Case

[57] ABSTRACT

The invention relates to a surgical instrument for ligation of internal tissues, such as hemorrhoids, in a cavity of the body by means of an elastic cord. The instrument comprises an inner front-cylinder (1) with the elastic cord (2) strained around its front end and a displaceable outer discharge-cylinder (3) arranged on the front-cylinder (1). At displacement the elastic cord (2) is pushed beyond the front-cylinder (1) and ligates the stem of a tissue (12) inserted in the front-cylinder (1). One of the two cylinders (1;3) is connected to a profiled tube (4) and the other cylinder (3;1) is connected to one end of a relatively stiff strip (5), which constitutes the actuating means (6) for the relative displacement of the cylinders. The strip is preferably formed into an actuating loop and the displacement is attained by pressing the actuating loop (6) towards the tube (4).

15 Claims, 1 Drawing Sheet

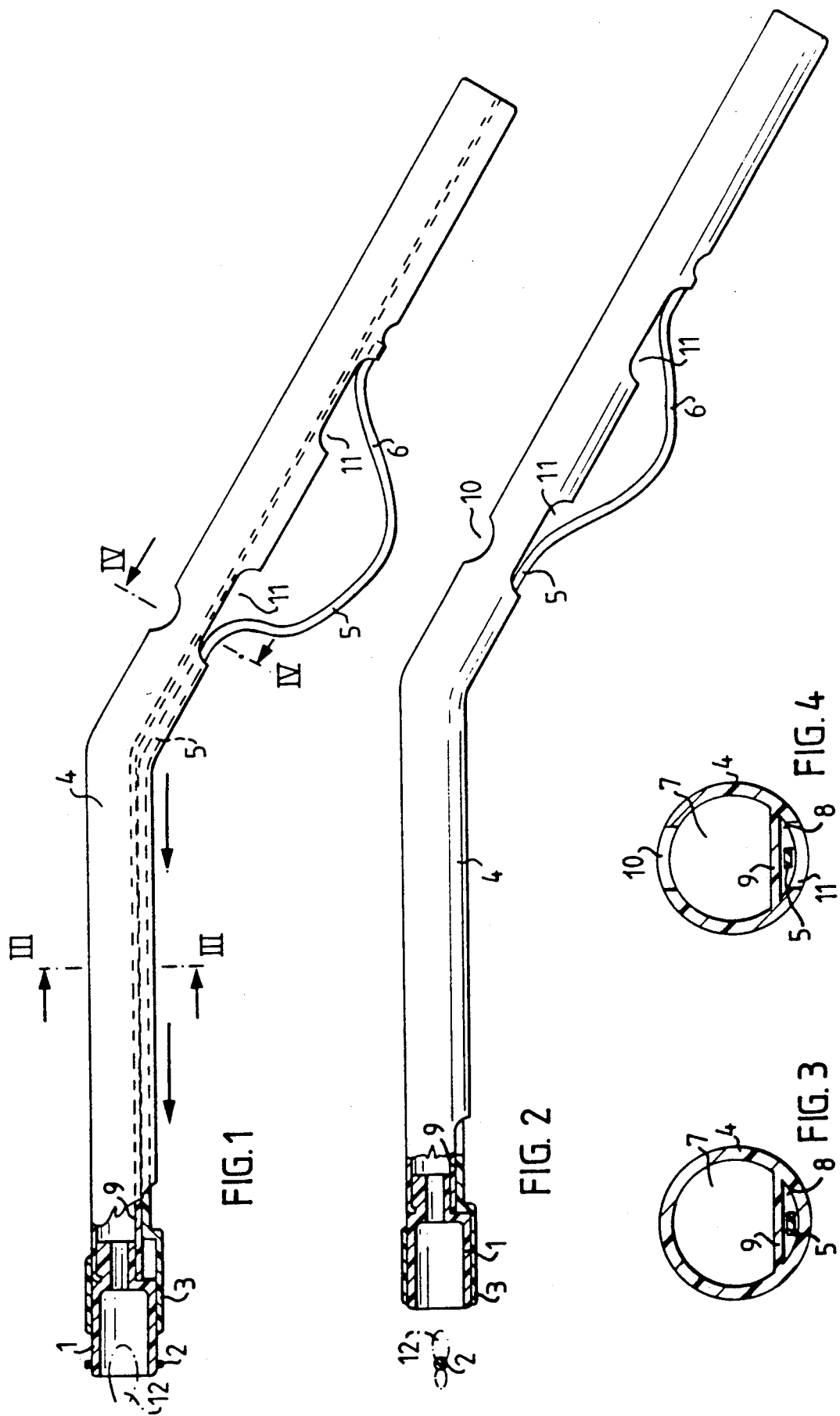

SURGICAL INSTRUMENT

This application is a continuation of application Ser. No. 544,039, filed on Jun. 26, 1990, now abandoned, which is a continuation of application Ser. No. 246,697 filed in Sep. 20, 1988, now abandoned.

FIELD OF THE INVENTION

The present invention relates to a surgical instrument for the ligating of internal tissues of a cavity in the human body by means of an elastic cord. The instrument comprises an inner front-cylinder with the elastic cord strained around its front end and a displaceable outer discharge-cylinder arranged on the front-cylinder. At displacement the elastic cord is pushed beyond the front-cylinder to close around the stem of a tissue which is inserted in the front-cylinder.

BACKGROUND OF THE INVENTION

During recent years requirements for the sterilization of surgical instruments have been intensified due to increased knowledge of the risks of infection in public health and sick care. The HIV-problems contribute to the enforcement of stricter requirements for sterilization, especially of instruments for rectal use.

Surgical instruments which are utilized to devitalize tissues, such as internal hemorroids, by ligation, a so-called elastic ligature, represent one type of proctologic instrument which is affected by these stricter requirements for sterilization. Different types of instruments for ligating of internal hemorrhoids are known. All these instruments are meant to be used several times, that is, they are designed to be re-utilized several times with a sterilization in between.

The method of sucking a hemorrhoid into a cylinder with an elastic cord mounted around it is previously known, e.g. from U.S. Pat. No. 4,257,419. A displaceable outer cylinder is arranged on the suction cylinder and an actuating element is adapted, via a transmission mechanism, to displace the outer cylinder in such a way that the cord is pushed beyond the suction cylinder, whereby it will enclose the hemorrhoid which is inserted in the suction cylinder.

U.S. Pat. No. 3,382,873 discloses a more simple construction of an instrument designed for the same purpose. This instrument is intended to be used together with a gripping instrument which is lead through the concentric cylinders to grip and introduce a hemorrhoid into the cylinders. When the actuating element is brought into force, the angled inner cylinder is displaced backwards along its longitudinal axis by means of interacting cam surfaces and the elastic cord is released. The hemorrhoid is introduced into the cylinders by means of the extra gripping instrument. This instrument is therefor not constructed to interact with a vacuum source.

U.S. Pat. No. 3,760,810 discloses several different embodiments of an instrument for the ligation of hemorrhoids. The embodiments all have in common that the instrument is made of two concentric tubes with an elastic cord arranged around the front part of one of the tubes and that one tube is displaceable on the other. One of these tubes is connected to a fixed handle and the other is connected to a movable actuating element, via a transmission mechanism. In one embodiment the instrument can be connected to a vacuum source, while in the other embodiments an interacting gripping tool must be utilized. One embodiment discloses an instrument (see FIG. 12-14) which permits one unit, comprising the two concentric tubes, to be disengaged from the handle. This unit can be exchanged and consequently one part of the instrument can be disposable. The previously known instruments have a number of disadvantages:

Instruments that necessitate interaction with a gripping instrument are difficult to handle since the operating surgeon must use both hands, one for the instrument and the other for the assisting tool. In addition, the proctoscope which is used for orientation in the cavity in the human body must be held by an assistant, which involves a difficult coordination between the instruments, with prolonged operation time as a consequence.

All previously known solutions disclose constructions which are complicated and contain a large number of interacting parts. The transmission mechanism between the activating element and the discharge-cylinder in particular contains several integral parts. The different parts are often made of metal. The known constructions are thus made for reutilization with a sterilization in between.

To make one part of the instrument disposable, as shown in U.S. Pat. No. 3,760,810 described above, implies that the different parts must be furnished with connecting devices, in this case a dovetailed guide connection, which makes the manufacturing complicated and the instrument more expensive. Furthermore, the part of the instrument which will be reutilized has to be sterilized between every utilization.

In conclusion, it can be claimed that none of the previously known instruments discloses a construction which makes it suitable as a disposable instrument.

SUMMARY OF THE INVENTION

The object of the present invention is to solve the above problems by providing a surgical instrument which is disposable. The instrument is made of a few simple parts which can be manufactured from simple materials. The instrument is easy to activate and utilize and is designed to be connected to a vacuum source.

The instrument is principally intended for the ligating of internal hemorrhoids but can also be used for the devitalization of mucous membrane tissues in other cavities of the human body.

A surgical instrument as described by way of introduction is according the invention characterized in that one cylinder is connected to a profiled tube and the other cylinder is connected to one end of a relatively stiff elongated strip, and that the strip constitutes actuating means for the relative displacement of the cylinders. As used in connection with the actuating strip, the term "relatively stiff" means that the elongated strip (or other elongated member) is stiff but flexible enough to bend in a direction perpendicular to its axis.

Other advantageous features of the invention will become apparent from the following description of embodiments of the invention and from the dependent claims.

The different parts of the disposable instrument are made of plastic material at a low cost per kilo and with a resistance to sterilization with ethylene oxide gas.

The profiled tube is made of a stiff, transparent, thermoformable and extrudable material, such as polyvinyl chloride.

The cylinder which is connected to the tube is made of a rigid and a stable material, which preferably also has low friction and a fusion temperature which is higher than the fusion temperature of the material of the profiled tube. One example of a material with these characteristics is polyamide.

The strip and the cylinder connected to the strip are made of strong material with low friction. Also for these parts polyamide is a suitable material.

The width of the strip to the thickness is in the ratio of 3:1 in order to ensure that the strip only bends in one direction.

BRIEF DESCRIPTION OF THE DRAWINGS

One embodiment of a surgical instrument according to the invention will be described in detail below with reference to the accompanying drawings, where FIG. 1 shows a side elevation of the instrument in a first position, with a partly sectional view through its front part, FIG. 2 shows the instrument in the same way as in FIG. 1 but in an actuated position, FIG. 3 shows an enlarged sectional view along the line III—III, FIG. 4 shows an enlarged sectional view along the line IV—IV.

DETAILED DESCRIPTION OF A PREFERRED EMBODIMENT OF THE INVENTION

A surgical instrument for the ligation of hemorrhoids is shown in its initial position in FIG. 1. The instrument comprises an angled profiled tube (4), which at its front end is connected with an inner front-cylinder (1) with an adapted and defined inner volume. An elastic cord (2) is strained around the front part of the cylinder (1).

The angled tube (4) is divided longitudinally by a partition wall 9 into two separate parts 7 and 8, see FIGS. 3 and 4. One part, the vacuum passage (7) of the tube, is designed to be connected to a vacuum source at the rear end. A restriction hole (10) is situated in the upper side of the tube in a position that is easy to reach by a finger (preferably the thumb) of the user when the hand grips the rear angled part of the tube while handling the instrument. The size of the hole is defined by the fact that it shall be capable of being covered by the finger. In the other part of the tube, the guiding passage (8), two guiding holes (11) are arranged at a distance from each other and are positioned in the rear angled part of the tube.

On the front-cylinder (1), see FIG. 1, an outer discharge-cylinder (3) is displaceably arranged, said discharge-cylinder having in its initial position, a backward position in relation to the front-cylinder (1). The discharge-cylinder (3) is connected to one end of a relatively stiff strip (5), which is arranged to run in the guiding passage (8) of the tube from the discharge-cylinder and up to the first guiding hole (11). The strip (5) is arranged to run outside the tube (4) between the two guiding holes (11), where it forms an actuating loop (6) by means of which the other end of the strip is connected to the rear part of the tube, for example by fusion.

THE OPERATION OF THE INVENTION

When operated, the instrument is connected to a vacuum source and is inserted into the cavity of the body. By covering the restriction hole (10) with a finger (the thumb), a vacuum is created in the front-cylinder (1), whereby a located hemorrhoid (12) can be sucked into the cylinder. By means of the remaining fingers of the hand the actuating loop (6) is subsequently pressed towards the tube (4). The strip (5), because it is relatively stiff, (5) thereby pushes the discharge-cylinder (3) forward on the front-cylinder (1) and the elastic cord (2) is released to ligate the base of the hemorrhoid to shut off its circulation. The restriction hole (10) can now be opened to counter-balance the vacuum in the front-cylinder (1) and the instrument can then be removed.

MODIFICATIONS OF THE INVENTION

The invention is in no way limited to the embodiment described above and several possible modifications of the invention are possible within the scope of the claims. One example is that the angled tube can be replaced with a straight tube. Instead of the restriction hole in the tube, the vacuum in the front-cylinder can be adjusted by a valve in the vacuum hose, which may be controlled, for example, by a foot-operated control. The rigid actuating strip can be connected to the front-cylinder instead of to the discharge-cylinder, the discharge-cylinder consequently being connected to the tube. In this embodiment the strip is activated by a tractive force for discharge of the elastic cord. The rear end of the strip can be free in a position between the guiding holes and preferably provided with a grippable knob or the like to allow displacement of the strip forwards and backwards when needed.

The vacuum in the front cylinder can be created manually, for example by connecting a disposable syringe, a rubber bladder or a bellows to the tube. In this embodiment a valve is used to control the vacuum in the front cylinder instead of the restriction hole. The rear end of the tube is preferably formed externally to be connected to a hose to a vacuum source and internally to be connected to a valve for controlling the vacuum in the front cylinder, preferably a three way valve. The syringe is preferably equipped with means for locking the plunger of the syringe in its extracted position. The bladder or bellows should for the same reason be equipped with a check valve both in inlet and outlet.

To operate the instrument with a manually operated vacuum source, the three way valve is connected to the end of the tube and the syringe, bladder or bellows is further connected to the valve. The valve is closed when the plunger of the syringe is operated to its extracted position where it is locked, or when the bladder or bellows is evacuated. The instrument is inserted into the cavity of the body with its front end close to the tissue that shall be removed. When the valve is opened a connection between the vacuum source and the front-cylinder is opened to create a vacuum in the front cylinder for insertion of a tissue. The actuating loop is activated for ligating the tissue. The valve can be opened to the atmospheric pressure before the instrument is withdrawn from the cavity.

I claim:

1. A surgical instrument for ligating internal tissues of a cavity in the human body by means of an elastic cord, said instrument comprising:
   an inner cylinder for retaining a stretched elastic cord about its front end;
   an outer discharge cylinder arranged about the inner cylinder and axially displaceable relative to the inner cylinder, wherein said discharge cylinder has a front end for selectively pushing an elastic cord beyond the front end of the inner cylinder to close around a tissue which is inserted in the inner cylinder;

an elongated support section extending from one of the cylinders to permit the instrument to be hand held;

a relatively stiff elongated actuating member connected to the other cylinder;

guide means for guiding said actuating member along said support section and for constraining radial movement of said actuating member, wherein said guide means includes an opening for exposing a section of said actuating member at a location spaced from said other cylinder, wherein the exposed section lies radially outward of the exterior of said support section at a location where the support section may be hand held with part of the hand over the exposed section; wherein the exposed section is moveable radially toward said support section responsive to squeezing of the hand about the support section and the exposed section; wherein the actuating member is axially displaceable in said guide means for moving said other cylinder; and wherein said guide means includes means, responsive to squeezing the exposed section radially inwardly, toward said support section, for causing said actuating member to move said other cylinder and thereby causing the discharge of an elastic cord from said inner cylinder.

2. A surgical instrument as recited in claim 1, wherein said actuating member is connected to said discharge cylinder for moving the discharge cylinder from a retracted position forward to an extended position for discharging an elastic cord.

3. A surgical instrument as recited in claim 2, wherein said support section comprises a tube connected to the inner cylinder.

4. A surgical instrument as recited in claim 3, wherein the actuating member has opposite ends, wherein one end is connected to said discharge cylinder, and wherein the guide means includes means for fixing the other end to said tube.

5. A surgical instrument as defined in claim 4, wherein said guide means form the exposed section of the actuating member into an actuating loop bowed out away from the tube when the discharge cylinder is in its retracted position.

6. A surgical instrument according to claim 5, wherein the actuating member is a strip.

7. A surgical instrument as defined in claim 5, wherein the exposed section of the actuating member is proximate to the said other end of the actuating member.

8. A surgical instrument according to claim 5, wherein all parts of the instrument are made of plastic material to form a disposable instrument.

9. A surgical instrument according to claim 3, wherein the guide means comprises an axial partition in said tube for defining a guide passage for directing the actuating member from said discharge cylinder along said tube, and said tube includes an opening communicating between the guide passage and the tube exterior for directing said actuating member out of the guide passage and tube to form the exposed section thereof.

10. A surgical instrument as define din claim 9, wherein the tube has an inlet end connected to said inner cylinder and an outlet and connectable to a vacuum source, and wherein the partition defines a vacuum passage extending from said inner cylinder to said distal end.

11. A surgical instrument as defined in claim 10, wherein the actuating member is a strip having opposite ends, wherein one end is connected to the discharge cylinder, wherein the strip extends along the guide passage and out of the tube opening, wherein the other end of the strip is fixed to the tube at a distance axially spaced from the tube opening, and wherein the strip is of a length such that, when the discharge cylinder is in a retracted position, the exposed portion of the strip bows outwardly to define an actuating loop.

12. A surgical instrument as defined in claim 11, wherein the tube includes a second opening and the actuating loop is formed between the two openings.

13. A surgical instrument as defined in claim 10, wherein said tube includes a ventilation hole communicating with the vacuum passage sized and located to be selectively covered with a finger when the tube is held to create vacuum in the vacuum passage.

14. An instrument for positioning and releasing a stretched elastic cord, said instrument comprising:

an inner cylinder for retaining a stretched elastic cord about its front end;

an outer discharge cylinder arranged about he inner cylinder and axially displaceable relative to the inner cylinder, wherein said discharge cylinder has a front end for selectively pushing an elastic cord beyond the front end of the inner cylinder to close around a tissue which is inserted in the inner cylinder;

an elongated support section extending from one of the cylinders to permit the instrument to be hand held;

a relatively stiff elongated actuating member connected to the other cylinder;

guide means for guiding said actuating member along said support section and for constraining radial movement of said actuating member, wherein said guide means includes an opening for exposing a section of said actuating member at a location spaced from said other cylinder, wherein the exposed section lies radially outward of the exterior of said support section at a location where the support section may be hand held with part of the hand over the exposed section; wherein the exposed section is moveable radially toward said support section responsive to squeezing of the hand about the support section and the exposed section; wherein the actuating member is axially displaceable in said guide means for moving said other cylinder; and wherein said guide means includes means, responsive to squeezing the exposed section radially inwardly, toward said support section, for causing said actuating member to move said other cylinder and thereby causing the discharge of an elastic cord from said inner cylinder.

15. An instrument according to claim 14, wherein said support section includes a first tubular portion extending axially from said one cylinder, and a second tubular section extending from said first tubular portion at an angle thereto; wherein said exposed section is located along part of said second tubular section; and wherein said guide means includes means for guiding said actuating member along said first and second tubular portions.

* * * * *